(12) United States Patent
Pylypchuk

(10) Patent No.: US 7,964,221 B2
(45) Date of Patent: Jun. 21, 2011

(54) COMPOSITION AND METHODS OF USE OF AN IMMUNOMODULATOR

(75) Inventor: Volodymyr Pylypchuk, Kiev (UA)

(73) Assignee: Immunitor USA, College Park, MD (US)

( * ) Notice: Subject to any disclaimer, the term of this patent is extended or adjusted under 35 U.S.C. 154(b) by 550 days.

(21) Appl. No.: 11/965,377

(22) Filed: Dec. 27, 2007

(65) Prior Publication Data

US 2008/0166435 A1 Jul. 10, 2008

Related U.S. Application Data

(60) Provisional application No. 60/877,631, filed on Dec. 29, 2006.

(51) Int. Cl.
*A61K 36/00* (2006.01)
*A61K 36/866* (2006.01)
*A61K 36/28* (2006.01)
*A61K 36/45* (2006.01)

(52) U.S. Cl. ......... 424/725; 424/744; 424/745; 424/764

(58) Field of Classification Search .................. None
See application file for complete search history.

(56) References Cited

U.S. PATENT DOCUMENTS 6,911,221 B2 * 6/2005 Li

OTHER PUBLICATIONS http://davesgarden.com/guides/pf/go/54506/. Dave's Garden: "PlantFiles: Torch Aloe, Tree Aloe, Mountain Bush Aloe, Krantz Aloe; Aloe arborescens". Downloaded from the world-wide-web on Aug. 24, 2010.*
http://www.plantnames.unimelb.edu.au/Sorting/Polygonum.html#aviculare. Multilingual Multiscript Plant Name Database: "Sorting Polygonum names". Downloaded from the world-wide-web on Aug. 24, 2010.*
http://plants.usda.gov/java/profile?symbol=ACMIO. United States Department of Agriculture; Natural Resources Conservation Services Plants Database: "*Archillea millefolium*". Downloaded from the world-wide-web on Aug. 24, 2010.*
http://www.desert-tropicals.com/Plants/Asteraceae/Echinacea_purpurea.html. Desert Tropicals© 1998-2005 Philippe Faucon: "Purple Coneflower". Downloaded from the world-wide-web on Aug. 24, 2010.*
http://www.issg.org/database/species/ecology.asp?si=1197&fr=1&sts=. Global Invaseive Species Database: "*Hypericum perforatum* (herb)".*
http://plants.usda.gov/java/profile?symbol=CEER5. United States Department of Agriculture; Natural Resources Conservation Services Plants Database: "*Centaurium erythraea*; European centaury". Downloaded from the world-wide-web on Aug. 24, 2010.*
http://www.naturalstandard.com/monographs/herbssupplements/crampbark.asp?. Natural Standard Monograph: (www.naturalstandard.com) Copyright © 2010. "Cramp bark (*Viburnum opulus*)". Downloaded from the world wide web on Aug. 24, 2010.*
http://plants.usda.gov/java/profile?symbol=VIOP. United States Department of Agriculture; Natural Resources Conservation Services Plants Database: "*Viburnum opulus*". Downloaded from the world-wide-web on Aug. 24, 2010.*
http://davesgarden.com/guides/pf/go/885/. Dave's Garden: PlantFiles: Dandelion, Lion's Tooth, Bitterwort, Chicoria, Fortune-Teller, Wild Endive, Puffball: Taraxacum officinale. Downloaded from the world wide web on Aug. 24, 2010.*
http://plants.usda.gov/java/profile?symbol=ACCA4. United States Department of Agriculture; Natural Resources Conservation Services Plants Database: "*Acorus calamus* L.". Downloaded from the world-wide-web on Aug. 24, 2010.*
http://en.wikipedia.org/wiki/Oregano. Wikipedia: "Oregano". Downloaded from the world-wide-web on Aug. 24, 2010.*
http://en.wikipedia.org/wiki/Marjoram. Wikipedia: "Majorum". Downloaded from the world-wide-web on Aug. 24, 2010.*
http://www.holisticonline.com/herbal-med/_Herbs/h37.htm. Holistic online.com: "Calendula". Downloaded from world wide web on Aug. 24, 2010.*
http://plants.usda.gov/java/profile?symbol=HIRH80. United States Department of Agriculture; Natural Resources Conservation Services Plants Database: "*Hippophae rhamnoides* L. seaberry". Downloaded from the world-wide-web on Aug. 24, 2010.*
http://en.wikipedia.org/wiki/Elecampane. Wikipedia: "Elecampane". Downloaded from world wide web on Aug. 24, 2010.*
http://www.henriettesherbal.com/. Henriette's Herbal Homepage: "Elecampane. *Inula helenium* L.". Downladed from world wide web on Aug. 25, 2010.*
http://plants.usda.gov/java/profile?symbol=POER81. United States Department of Agriculture; Natural Resources Conservation Services Plants Database: "*Potentilla erecta* (L.) Raeusch. erect cinquefoil". Downloaded from the world-wide-web on Aug. 24, 2010.*
http://plants.usda.gov/java/profile?symbol=PLMA2. United States Department of Agriculture; Natural Resources Conservation Services Plants Database: "*Plantago major* L. common plaintain". Downloaded from the world-wide-web on Aug. 25, 2010.*
http://en.wikipedia.org/wiki/Artemisia_absinthium. Wikipedia: "*Artemisia absinthium*". Downloaded from the world-wide-web on Aug. 25, 2010.*
http://plants.usda.gov/java/profile?symbol=RHRO3. United States Department of Agriculture; Natural Resources Conservation Services Plants Database: "*Rhodiola rosea* L. roseroot stonecrop". Downloaded from the world-wide-web on Aug. 25, 2010.*
http://plants.usda.gov/java/profile?symbol=GNUL. United States Department of Agriculture; Natural Resources Conservation Services Plants Database: "*Gnaphalium uliginosum* L. marsh cudweed". Downloaded from the world-wide-web on Aug. 25, 2010.*

(Continued)

*Primary Examiner* — Michele Flood
(74) *Attorney, Agent, or Firm* — Dykema Gossett PLLC

(57) ABSTRACT

A composition including one or more of elecampane rhizome (*Inula* sp.), fennel fruit (*Foeniculum* sp.), juniper berry (*Juniperus* sp.), licorice root (*Glycyrrhiza* sp.), oregano herb (*Oreganum* sp.), marigold flowers (*Calendula* sp.), rose hips (*Rosa* sp.), and thyme (*Thymus* sp.), or an extract thereof. The composition is useful for treating infectious diseases, for example viral and microbial infections, and for reducing the toxic effects of chemotherapeutic agents.

1 Claim, 1 Drawing Sheet

Figure 1:
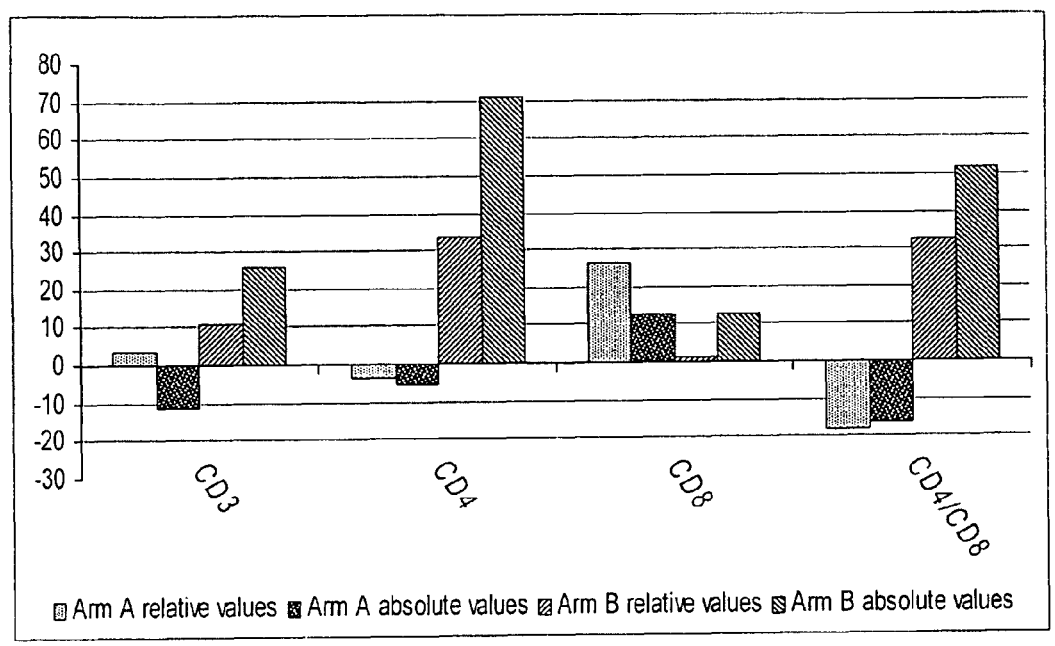

OTHER PUBLICATIONS http://www.mdidea.com/products/new/new01101.html. MDidea: "Licorice:Glycyrrhiza Glabra, Licorice Root Extract". Downloaded from the world-wide-web on Aug. 25, 2010.* http://plants.usda.gov/java/profile?symbol=FOVU. United States Department of Agriculture; Natural Resources Conservation Services Plants Database: "*Foeniculum vulgare* Mill. sweet fennel". Downloaded from the world-wide-web on Aug. 25, 2010.* http://en.wikipedia.org/wiki/Chaga_mushroom. Wikipedia: "Chaga mushroom". Downloaded from the world-wide-web on Aug. 25, 2010.* http://plants.usda.gov/java/profile?symbol=THVU. United States Department of Agriculture; Natural Resources Conservation Services Plants Database: "*Thymus vulgaris* L. garden thyme". Downloaded from the world-wide-web on Aug. 25, 2010.* http://www.agroatlas.ru/en/content/weeds/Bidens_tripartita/. AgroAtlas:"*Bidens tripartite* L.-Spanish Needles". Downloaded from the world-wide-web on Aug. 25, 2010.* http://en.wikipedia.org/wiki/Salvia_officinalis. Wikipedia: "*Salvia officinalis*". Downloaded from the world-wide-web on Aug. 25, 2010.* http://plants.usda.gov/java/profile?symbol=ROCA3. United States Department of Agriculture; Natural Resources Conservation Services Plants Database: "*Rosa canina* L. dog rose". Downloaded from the world-wide-web on Aug. 25, 2010.* http://plants.usda.gov/java/profile?symbol=JUCO6. United States Department of Agriculture; Natural Resources Conservation Services Plants Database: "*Juniper communis* L. common juniper". Downloaded from the world-wide-web on Aug. 25, 2010.* http://en.wikipedia.org/wiki/Berberis_vulgaris. Wikipedia: "*Berberis vulgaris*". Downloaded from the world-wide-web on Aug. 25, 2010.* http://www.herbalremedies.com/chicoryroot-information.html. Herbal Remedies.com: "Chicory root / Cichorium intybus / Blue Dandelion / Blue-Sailors / Coffeeweed / Endive / Garden Chicory / Succory / Wild Chicory / Wild Succory Information". Downloaded from the world-wide-web on Aug. 25, 2010.* http://plants.usda.gov/java/profile?symbol=COSA. United States Department of Agriculture; Natural Resources Conservation Services Plants Database: "*Coriandrum sativum* L. coriander". Downloaded from the world-wide-web on Aug. 25, 2010.* http://plants.usda.gov/java/profile?symbol=ZEMA. United States Department of Agriculture; Natural Resources Conservation Services Plants Database: "*Zea mays* L. corn". Downloaded from the world-wide-web on Aug. 25, 2010.* http://www.ars-grin.gov/cgi-bin/npgs/html/taxon.pl?4247. United States Department of Agriculture Agricultural Research Service:"*Aronia melanocarpa*". Downloaded from the world-wide-web on Aug. 25, 2010.* http://en.wikipedia.org/wiki/Fragaria_vesca. Wikipedia: "*Fragaria vesca*". Downloaded from the world-wide-web on Aug. 25, 2010.* http://plants.usda.gov/java/profile?symbol=CHMA2. United States Department of Agriculture Agricultural Research Service:"*Chelidonium majus*". Downloaded from the world-wide-web on Aug. 25, 2010.* http://www.holisticonline.com/herbal-med/_Herbs/h213.htm. Holistic online.com. "Celandinine". Downloaded from world wide web on Aug. 25, 2010.* http://en.wikipedia.org/wiki/Helichrysum_arenarium. Wikipedia: "*Helichrysum arenarium*". Downloaded from world wide web on Aug. 26, 2010.*

Mabberley, D. J. The Plant-Book: A portable dictionary of the vascular plants, 2nd Edition (1997). Cambridge University Press, United Kingdom, pp. 360,361 and 508-511.*

* cited by examiner

COMPOSITION AND METHODS OF USE OF AN IMMUNOMODULATOR

CROSS REFERENCE TO RELATED APPLICATIONS

This application claims the benefit of U.S. Provisional Application No. 60/877,631, filed on Dec. 29, 2006, for all purposes. The entirety of this application is hereby incorporated by reference.

FIELD OF THE INVENTION

The invention regards medicinal herb compositions and their use in patient treatment.

BACKGROUND OF THE DISCLOSURE

Antiretroviral drug resistance, drug toxicity, and adherence are major concerns in the clinical management of HIV infection. On the other hand, the immune activation caused by immune reaction to HIV, is now recognized as a major cause of depletion of $CD4^+$ (CD4) T-cells and resulting immunodeficiency. In fact, African monkeys, the natural hosts of simian immunodeficiency virus have adapted to this retrovirus by blocking immune activation and thus remaining healthy. An optimal therapeutic solution would be an effective and safe immunotherapy that could regulate the immune response in a manner favorable to a host.

Dzherelo is an oral immunomodulating agent produced from 26 plant materials by the inventor. It contains concentrated extracts from medicinal plants. In vitro studies on cultured thymocytes and epithelial thymic cells have shown that Dzherelo can induce synthesis of serum thymic factor and other substances with thymus like activity. Experiments on laboratory animals demonstrated the restoration of endocrine function and increase of thymus weight after partial thymectomia. It has been successfully used in the past for the therapy of various infectious diseases of viral origin such as herpes and Epstein-Barr viruses. Prior evidence indicates the tendency of Dzherelo to restore suppressed immunity characteristic of chronic bacterial infections and malignant diseases. Furthermore, Dzherelo has shown efficacy in treatment of autoimmune diseases.

Pilot trials conducted by us in HIV-infected individuals have shown that Dzherelo is safe, can increase the total and CD4 lymphocyte counts, and reduce the incidence of opportunistic infections. In addition it appeared to have a favorable effect in diminishing the toxicity of antiretroviral drugs.

Dzherelo is a complex mixture, however. An effective composition having fewer components would be desirable.

SUMMARY OF THE DISCLOSURE

We now present a simplified herbal composition prepared from essentially eight plant materials or extracts thereof. Surprisingly, this simpler version, termed composition No. 1, had an equal effect as one that contained a higher number of herbs.

In one aspect the inventors have identified a useful composition consisting essentially of plant material from *Inula* sp., *Foeniculum* sp., *Juniperus* sp., *Glycyrrhiza* sp., *Oreganum* sp., *Calendula* sp., *Rosa* sp., and *Thymus* sp., or an extract thereof, or a combination of the extracts.

In another aspect, the inventors have found a method of treating a subject having an infectious disease comprising administering a composition comprising at least one plant material selected from the group consisting of *Inula* sp., *Foeniculum* sp., *Juniperus* sp., *Glycyrrhiza* sp., *Oreganum* sp., *Calendula* sp., *Rosa* sp., and *Thymus* sp., or an extract thereof, or a combination of the extracts, whereby liver function or incidence of adverse events is improved.

In yet another aspect, the inventors have found a method of ameliorating adverse effects of chemotherapy in a subject in need thereof comprising administering a composition comprising plant material comprising *Inula* sp., *Foeniculum* sp., *Juniperus* sp., *Glycyrrhiza* sp., *Oreganum* sp., *Calendula* sp., *Rosa* sp., or *Thymus* sp., or a combination thereof, or extracts thereof or a combination of extracts thereof.

In another aspect, the invention is a method of treating disease, including infectious viral disease.

We evaluated the clinical benefit of the composition No. 1 of the present invention in comparison to standard ART in a multicenter trial conducted at four regional hospitals in Ukraine. Here we present data from a 32-week, open label, three-arm trial in 70 HIV-infected individuals who were treated either with zidovudine (AZT), lamividine (3TC), and efavirenz (EFV), or with AZT/3TC/EFV in combination with the composition of the present invention, or the composition of present invention alone, assigned to arms A, B, and C, respectively.

Data on treatment of patients suffering from tuberculosis is also presented separately.

An immunomodulating agent has been evaluated in 70 HIV-infected individuals who were divided into three treatment arms: the first arm, serving as a control, received standard antiretroviral therapy (ART), that is, zidovudine/lamividine/efavirenz (AZT/3TC/EFV); second, AZT/3TC/EFV plus the composition of the present invention; and third, the composition of present invention alone which was given orally, twice daily. During 32 weeks of follow-up CD4 cell counts increased progressively in all arms, reaching +102, +190, and +175 cells/mm$^3$, in arms A, B, and C, respectively. The proportion of patients who experienced adverse events attributable to study medication was 65%, 24%, and 5% in arms A, B, and C, respectively. The composition of the present invention appears to attenuate hepatic toxicity in patients receiving ART as determined by liver function test. Mean baseline values for ALT aminotransferase were 36, 62 and 72 U/L in arms A, B, and C, respectively. At study conclusion, ALT values had risen to a mean 78 U/L in arm A but declined to 38 and 31 U/L in arms B and C, respectively. The composition of the present invention was also useful in correcting AIDS-associated wasting. The average weight gain was 1.4, 6.9, and 5.1 kg for arms A, B, and C. These clinical data indicate that the composition of present invention is very safe and has beneficial clinical effect in the treatment of HIV and AIDS.

Another embodiment of the invention comprises a somewhat more complex combination of plant materials useful, e.g., for treatment of tuberculosis patients. This embodiment is termed composition No. 2.

The complex combination ("No. 2") of herbal materials has superior efficacy for some illnesses than when said materials are used alone. Such a combination can have following ingredients, which can be administered together or as three sets of ingredients. The first set (Composition No. 2 set No. 1) will essentially contain medicinal plants such as Aloe (*Aloe arborescens*), Common knotgrass (*Polygonum aviculare*), Yarrow (*Achillea millefolium*), Purple coneflower (*Echinacea purpurea*), St. John's Wort (*Hypericum perforatum*), Centaury (*Centaurium erythraea*), Snowball tree berries (*Viburnum opulus*), Nettle (*Urtica dioica*), Dandelion (*Taraxacum officinale*), Sweet-sedge (*Acorus calamus*), Oregano (*Oreganum majorana*), Marigold (*Calendula officinalis*), Seabuckthorn berries (*Hippophae rhamnoides*), Elecampane (*Inula helenium*), Tormentil (*Potentilla erecta*), Greater plantain (*Plantago major*), Wormwood (*Artemisia* sp.), Siberian golden root (*Rhodiola rosea*), Cudweed (*Gnaphalium uliginosum*), Licorice (*Glycyrrhiza glabra*), Fennel (*Foeniculum vulgare*), Chaga (*Inonotus obliquus*), Thyme (*Thymus vulgaris*), Three-lobe Beggarticks (*Bidens tripartite*), Sage (*Salvia officinalis*), Dog rose (*Rosa canina*), and Juniper berries (*Juniperus communis*).

The second set (No. 2, set No. 2) essentially contains flowers of Immortelle (*Helichrysi arenarii*), Barberry roots (*Berberis vulgaris*), Chicory roots (*Cichorium intybus*), Coriander seeds (*Coriandrum sativum*), Marigold (*Calendula officinalis*), Wormwood (*Artemisia* sp.), and Maize cores with stigmas (*Zea mays*).

The third set (No. 2, set No. 3) essentially contains Barberry roots (*Berberis vulgaris*), Aronia berries (*Aronia melanocarpa*), St. John's Wort (*Hypericum perforatum*), Centaury (*Centaurium erythraea*), Nettle (*Urtica dioica*), Common knotgrass (*Polygonum aviculare*), Wild strawberry leaves (*Fragaria vesca*), Greater celandine (*Chelidonium majus*), and Immortelle (*Helichrysi arenarii*).

In one aspect, the composition can be simplified by eliminating duplicate ingredients.

Such a multi-herb combination of three separate formulations may have additional individual ingredients as will become evident from the detailed disclosure of the invention. The compositions can be used alone or further combined with first line TB drugs comprising isoniazid (H), rifampicin (R), ethambutol (E), pyrazinamide (Z), and/or streptomycin (S). Also they can be combined further with second-line TB drugs including aminoglycosides such as: amikacin, or kanamycin; polypeptides including capreomycin, viomycin, or enviomycin; fluoroquinolones such asciprofloxacin, or moxifloxacin; thioamides such as ethionamide, or prothionamide; cycloserine; and/or para-aminosalicylic acid. Other TB drugs that can be used in further combination are: rifabutin; clarithromycin; linezolid; thioacetazone; thioridazine; arginine; vitamin D; and/or R207910 and/or derivatives thereof.

Other embodiments relate to combinations of components. One embodiment (termed composition No. 3) relates to compositions that include, as a first component, Aloe (*Aloe arborescens*), and as a second component at least one member selected from the group consisting of Common knotgrass (*Polygonum aviculare*), Yarrow (*Achillea millefolium*), Purple coneflower (*Echinacea purpurea*), St. John's Wort (*Hypericum perforatum*), Centaury (*Centaurium erythraea*), Snowball tree berries (*Viburnum opulus*), Nettle (*Urtica dioica*), Dandelion (*Taraxacum officinale*), Sweet-sedge (*Acorus calamus*), Oregano (*Oreganum majorana*), Marigold (*Calendula officinalis*), Seabuckthorn berries (*Hippophae rhamnoides*), Elecampane (*Inula helenium*), Tormentil (*Potentilla erecta*), Greater plantain (*Plantago major*), Wormwood (*Artemisia* sp.), Siberian golden root (*Rhodiola rosea*), Cudweed (*Gnaphalium uliginosum*), Licorice (*Glycyrrhiza glabra*), Fennel (*Foeniculum vulgare*), Chaga (*Inonotus obliquus*), Thyme (*Thymus vulgaris*), Three-lobe Beggarticks (*Bidens tripartite*), Sage (*Salvia officinalis*), Dog rose (*Rosa canina*), and Juniper berries (*Juniperus communis*). Composition No. 3 can be combined with Composition No. 2, set 2 and/or set 3.

Another embodiment (termed composition No. 4) relates to compositions that include, as a first component, the active ingredient from Aloe and as a second component at least one active ingredient isolated from the group of medicinal plants: Common knotgrass (*Polygonum aviculare*), Yarrow (*Achillea millefolium*), Purple coneflower (*Echinacea purpurea*), St. John's Wort (*Hypericum perforatum*), Centaury (*Centaurium erythraea*), Snowball tree berries (*Viburnum opulus*), Nettle (*Urtica dioica*), Dandelion (*Taraxacum officinale*), Sweet-sedge (*Acorus calamus*), Oregano (*Oreganum majorana*), Marigold (*Calendula officinalis*), Seabuckthorn berries (*Hippophae rhamnoides*), Elecampane (*Inula helenium*), Tormentil (*Potentilla erecta*), Greater plantain (*Plantago major*), Wormwood (*Artemisia* sp.), Siberian golden root (*Rhodiola rosea*), Cudweed (*Gnaphalium uliginosum*), Licorice (*Glycyrrhiza glabra*), Fennel (*Foeniculum vulgare*), Chaga (*Inonotus obliquus*), Thyme (*Thymus vulgaris*), Three-lobe Beggarticks (*Bidens tripartite*), Sage (*Salvia officinalis*), Dog rose (*Rosa canina*), and Juniper berries (*Juniperus communis*). Composition No. 4 can be combined with Composition No. 2, sets 2 and/or 3.

BRIEF DESCRIPTION OF THE TABLES AND FIGURES

Table 1 is a summary of characteristics of patients at the initiation of a three-arm study to evaluate the effect of the composition No. 1 of the present invention on AIDS patients.

Table 2 shows the percentage of patients with clinical adverse events considered as possibly related to treatment and of moderate or severe intensity. The study is the evaluation of the effect of the composition No. 1 of the present invention on AIDS patients.

Table 3 shows the percentage of patients presenting with clinical opportunistic infections or co-infection defined events during a 32-week treatment period. The study is the evaluation of the effect of the composition No. 1 of the present invention on AIDS patients.

Table 4 describes changes in CD4 lymphocyte counts, body weight and alanine transaminase (ALT) in patients with HIV.

Table 5 shows a summary of the effect of composition No. 1 on viral load decrease Table 6 describes effect on body weight in patients with TB.

Table 7 is a summary of results of treatment of drug-resistant TB patients.

Table 6 describes radiological findings of TB therapy in AIDS patients who have TB.

Table 8 shows culture and radiological findings in TB/HIV co-infected patients.

Table 9 shows the effect on culture conversion and cavitary and miliary forms of TB.

Table 10 shows the effectiveness of herbal combination in patients with multi-drug resistant tuberculosis (MDR), extensively drug resistant TB (XDR), and in HIV/TB co-infection.

FIG. 1 shows changes in T-lymphocyte counts relative to baseline values.

DETAILED DESCRIPTION

The terms "medicinal plant," "herb," and "herbal," as used to describe the components of the invention, refer to materials of plant origin and can include without limit the leaves, stems, flowers, roots, and other plant parts, whether fresh or preserved. A preferable method of preservation of herbs is by drying. In one aspect, the terms can refer to the leaves.

As used herein, an extract refers to the soluble phase of a mixture comprising an aqueous organic solvent containing one or more desired medicinal plants at a proportion needed to extract the active principles of the herb.

The term "extracts," as used to describe the invention refers to extraction of useful components from herbs. Any method of extraction known in the art can be used. A preferred method of extraction is to mix a quantity of herb with a physiologically compatible solvent for at least a few minutes, a few hours, or some days.

In one aspect, the solvent is a physiologically compatible organic solvent. Any physiologically compatible organic solvent can be used, including, but not limited to ethyl alcohol, isopropyl alcohol, glycerol, acetone, dimethyl sulfoxide, acetic acid, butyric acid, citric acid, ethyl acetate, combinations thereof, and aqueous versions thereof A preferred physiologically compatible organic solvent is ethyl alcohol. Aqueous ethyl alcohol is more preferred, comprising, for example, 5% water and 95% ethyl alcohol.

Any ratio of physiologically compatible solvent to herb can be used. In one aspect, a ratio of from 1:1 to 1:10, by weight, is used.

Preferred physiologically compatible organic solvents are minimally toxic. By example, ethyl alcohol in the amounts used in the therapy of the invention is considered minimally toxic.

The compositions of the invention show surprising and beneficial immunomodulatory effects.

The compositions of the invention can be prepared with any amount of an herb in relation to another herb. In one aspect, each herb is present in an equal amount by weight. In another aspect, one herb is present at least ten times the amount of another herb. In yet another aspect, one herb is present at one to ten times the amount of another herb. In still another aspect, one herb is present at twice the amount of extract of another herb.

The compositions of the invention can also be prepared from extracts of herbs. In one aspect each extract is present in an equal amount by volume. In another aspect, an extract of one herb is present at more than ten times the amount of an extract of another herb. In yet another aspect, an extract of one herb is present at one to ten times the amount of extract of another herb. In still another aspect, an extract of one herb is present at twice the amount of extract of another herb.

The preferred dose can vary from one drop in new-born baby to 10-20 drops in adolescent and from 10 to 150 or more drops in an adult. The preferred range is between 10 to 50 drops once or twice per day. The most preferred route is oral although topical application is equally suitable. One skilled in the art can freely use other methods of delivery, and such methods are within a skill of a practitioner that can be experimentally determined by a routine practice without undue experimentation. One standard drop of an aqueous alcohol extract is about 0.03 ml.

The herbs are typically dried and ground to a fine powder. The composition can be an intimate mixture of powders that are formulated suitably such as pills or tablets. Such pills can be made directly from powdered plants or formulated from alcohol, for example, and water extracts by reduction according to established procedures well-known in the art procedures. The preferred extraction method is water or alcohol or water-alcohol mixture either simultaneously or in consequent subsequent steps as deemed necessary. The proportions of herbs to be mixed together generally range from about 1% to about 20% by weight of the composition, more preferably about 3% to about 5% by weight of the composition. The amount of alcohol is anywhere between 10-60% by weight if included at all in the present compositions.

In one aspect, the composition comprises a dried extract.

In one aspect, the following herbs in aqueous alcohol extracts are preferred: marigold flowers (*Calendula officinalis*), elecampane rhizome (*Inula helenium*), seabuckthorn fruit (*Hippophae rhamnoides*), potentilla rhizome (*Potentilla erecta*), fennel fruit (*Foeniculum vulgare*), rhodiola rosea root (*Rhodiola rosea*), rose hips (*Rosa canina*), licorice root (*Glycyrrhiza glabra*), juniper fruit (*Juniperus communis*), knotgrass (*Paspalum distichum*), aloe leaf (Aloe vera), yarrow (*Achillea millefolium*), nettle leaf (*Urtica dioica*), St-Johns worth (*Hypericum perforatum*), plantain leaf (*Plantago major*), centaury (*Centaurium erythraea*), salvia leaf (*Salvia divinorum*), oregano herb (*Oreganum majorana*), birch (*Betula pendula*), wormwood (*Artemisia sp.*,), flagroot rhizome (*Acorus calamus*), cudweed (*Gnaphalium uliginosum*), echinacea root (*Echinacea angustifolia*), thyme (*Thymus serpyllum*), dandelion rhizome (*Taraxacum officinale*), burmarigold (*Bidens tripartite*).

Other plants equally suitable and which can be added as ingredients of the instant invention can be selected from the group including but not limited to *Adina piluifera, Agrimonia eupatoria, Arbutus unedo, Arctostaphylos uva-ursi, Artocarpus heterophyllus, Catalpa bignoniodes, Catharanthus roseus, Chimaphila umbellata, Cornusfiorida, Cornus officinalis, Crataegus cuneata, Crataegus laevigata, Crataegus pinnatifida, Cryptostegia grandifolia, Elaeagnus pungens, Eriobotrya japonica, Eucalyptus citriodora, Forsythia suspensa, Gaultheria fragrantissima, Glechoma hederacea, Hedyotis diffusa, Helichrysum angustifolium, Humulus lupulus, Hyssopus officinalis, Ilex paraguariensis, Lavandula angustifolia, Lavandula latifolia, Leonurus cardiaca, Ligustrum japonicum, Limonia acidissima, Lycopus europeus, Malus domestica, Marubium vulgare, Melaleuca leucadendra, Melissa officinalis, Mentha spicata, Mentha x rotundifolia, Monarda didyma, Nerium oleander, Ocimum basilicum, Ocimum basilicum, Ocimum basilicum, Ocimum baslicum, Ocimum canum, Origanum majorana, Origanum vulgare, Plantago asiatica, Plantago major, Plectranthus amboinicus, Prunell vulgaris, Prunella vulgaris, Prunus cerasus, Prunus laurocerasus, Prunus persica, Prunus serotina spp serotina, Psidium guajava, Punica granatum, Pyrus communis, Rhododendron dauricum, Rhododendron ferrugineum, Rhododendron ponticum, Rosmarinus officinalis, Rubus fruticosus, Salvia officinalis, Salvia sclarea, Salvia triloba, Sambucus nigra, Sanguisorba officinalis, Satureja hortensis, Satureja montana, Sorbus aucubaria, Syring a vulgaris, Teucrium chamaedrys Teucrium polium, Teucrium spp, Thevetia peruviana, Thymus serpyllum, Thymus vulgaris, Uncaria tomentosa, Vaccinium corymobosum, Vaccinium myrtillus, Vaccinium vitis idaea, Verbena officinalis, Viburnum opulus var. opulus, Viburnum prunifolium, Vinca minor* or *Zizyphus jujuba*. Similarly, oleanolic acid is found in *Achyranthes aspera, Achyranthes bidentiata, Adina piluifera, Ajpocynum cannabinum, Akebia quinata, Allium cepa, Allium sativum, Arctostaphylos uva-ursi, Calendula officinalis, Catharanthus roseus, Centaurium erythraea, Chenopodium album, Citrullus colocynthis, Cnicus benedictus, Cornus officinalis, Crataegus pinnatifida Cyperus rotundus, Daemonorops draco, Diospyros kaki, Elaeagnus pungens, Eleutherococcus senticosus, Eriobotrya japonica, Eugenia caryophyllata, Forsythia suspensa, Glechoma hederacea, Harpagophtum procumbens, Hedera helix, Hedyotis diffusa, Helianthus annuus, Hemsleys amabilis, Humulus lupulus, Hyssopus officinalis, Ilex rotunda, Lavandula latifolia, Leonurus cardiaca, Ligustrum japonicum, Ligustrum lucidum, Liquidambar orientalis, Liquidambar styraciflua, Loranthus parasiticus, Luffa aegyptiaca, Melaleuca leucadendra, Melissa officinalis, Mentha spicata, Mentha x rotundifolia, Momordica cochinchinensis, Myristica fragrans, Myroxylon balsamum, Nerium oleander, Ocimum suave, Ociumum basilicum, Olea europaea, Origanum majorana, Origanum vulgare, Paederia scandens, Panax ginseng, Panax japonicus, Panax quinquefolius, Patrinia scabiosaefo-* lia, *Phytolacca americana, Plantago major, Plectranthus amboinicus, Prunella vulgaris, Prunus cerasus, Psidium guajava, Pulsatilla chinenisis, Quisqualis indica, Rosmarinus officinalis, Salvaia officinalis, Salvia sclarea, Salvia triloba, Sambucus nigra, Satureja hortensis, Satureja montana, Swertia chinensis, Swertia diluta, Swertia mileensis, Syzygium aromaticum, Thymus serpyllum, Thymus vulgaris, Trachycarpus fortunei, Uncaria tomentosa, Vaccinium corymbosum, Vaccinium myrtillus, Viburnum prunifolium, Viscum album, Vitis vinifera,* and *Zizyphus jujuba.* The preferred botanical sources for ursolic acid is a member selected from the group consisting of *Ligustrum japonicum, Plantago asiatica, Plantago major, Prunus species, Uncaria tomentosa, Zizyphus jujuba, Cornus officinalis, Eucalyptus citriodora, Forsythia suspensa, Lavandula latifolia, Malus domestica, Nerium oleander, Ocimum baslicum, Punica granatum, Pyrus communis, Rosmarinus officinalis, Salvia triloba, Sorbus aucubaria, Vaccinium myrtillus, Vaccinium vitis-idaea, Viburnum opulus* var. *opulus,* and *Zizyphus jujuba.*

EXAMPLES

The following examples illustrate aspects of the invention, but do not limit the scope. The scope of the invention is defined by the claims.

Example 1

Preparation of an Exemplary Herb Extract No. 1

One kilogram of each of the following dried herbs is separately mechanically pulverized: *Inula helenium, Foeniculum vulgare, Juniperus communis, Glycyrrhiza glabra, Oreganum majorana, Calendula officinalis, Rosa canina,* and *Thymus serpyllum.* Each of the powdered herbs is separately mixed and suspended in 5 liters of 95% aqueous ethyl alcohol with occasional agitation for two days. Each suspension is decanted, the respective supernate is filtered through a paper filter, and the extract is collected. Each extract is stored in dark bottles at about 20° C. for up to a year.

To prepare a therapeutic mixture, 500 ml of each extract is combined.

Example 2

Preparation of an Exemplary Herb Extract No. 2

For set No. 1 of Composition No. 1, one kilogram of each of the following dried herbs is separately ground to a powder: Aloe (*Aloe arborescens*), Common knotgrass (*Polygonum aviculare*), Yarrow (*Achillea millefolium*), Purple coneflower (*Echinacea purpurea*), St. John's Wort (*Hypericum perforatum*), Centaury (*Centaurium erythraea*), Snowball tree berries (*Viburnum opulus*), Nettle (*Urtica dioica*), Dandelion (*Taraxacum officinale*), Sweet-sedge (*Acorus calamus*), Oregano (*Oreganum majorana*), Marigold (*Calendula officinalis*), Seabuckthorn berries (*Hippophae rhamnoides*), Elecampane (*Inula helenium*), Tormentil (*Potentilla erecta*), Greater plantain (*Plantago major*), Wormwood (*Artemisia* sp.), Siberian golden root (*Rhodiola rosea*), Cudweed (*Gnaphalium uliginosum*), Licorice (*Glycyrrhiza glabra*), Fennel (*Foeniculum vulgare*), Chaga (*Inonotus obliquus*), Thyme (*Thymus vulgaris*), Three-lobe Beggarticks (*Bidens tripartite*), Sage (*Salvia officinalis*), Dog rose (*Rosa canina*), and Juniper berries (*Juniperus communis*). The powdered herbs are combined and suspended in 100 liters of 90% ethyl alcohol 10% distilled water. The suspension is agitated twice daily for three days. The suspension is then allowed to settle and the supernate filtered to produce the extract, which is stored in dark bottles.

For set No. 2 of Composition No. 2, one kilogram of each of the following dried materials is separately ground to a powder: flowers of Immortelle (*Helichrysi arenarii*), Barberry roots (*Berberis vulgaris*), Chicory roots (*Cichorium intybus*), Coriander seeds (*Coriandrum sativum*), Marigold (*Calendula officinalis*), Wormwood (*Artemisia* sp.), and Maize cores with stigmas (*Zea mays*). The powdered herbs are combined and suspended in 30 liters of 90% ethyl alcohol/10% distilled water. The suspension is agitated twice daily for three days. The suspension is then allowed to settle and the supernate filtered to produce the extract, which is stored in dark bottles.

For set No. 3 of Composition No. 2, one kilogram of each of the following dried materials is separately ground to a powder: Barberry roots (*Berberis vulgaris*), Aronia berries (*Aronia melanocarpa*), St. John's Wort (*Hypericum perforatum*), Centaury (*Centaurium erythraea*), Nettle (*Urtica dioica*), Common knotgrass (*Polygonum aviculare*), Wild strawberry leaves (*Fragaria vesca*), Greater celandine (*Chelidonium majus*), and Immortelle (*Helichrysi arenarii*). The powdered herbs are combined and suspended in 40 liters of 90% ethyl alcohol/10% distilled water. The suspension is agitated twice daily for three days. The suspension is then allowed to settle and the supernate filtered to produce the extract, which is stored in dark bottles.

The extracts are stored for up to a year at 15 to 24° C. To produce a therapeutic solution, two liters of set No. 1 is combined with one liters each of set No. 2 and set No. 3.

Example 3

Patient Population—HIV Studies

In this trial, 70 male or female adults with HIV/AIDS were enrolled. See Table 1. Most of them were hepatitis virus C (HCV) co-infected, with a significant proportion of them suffering from alcohol abuse or/and drug addiction. Significant metabolic disorders and underlying hepatic injury caused by chronic alcohol, drug addiction, and hepatitis co-infection were common for this study cohort. At study initiation 21% had active opportunistic infections and 71% had grade 3 or more laboratory or clinical abnormalities. Patients were divided into three arms, with comparable baseline characteristics. All participants were antiretroviral drug naive. Each participant provided an informed consent and was free to withdraw from the study at any time. All patients were given symptomatic therapy for opportunistic infections if required. The trial was designed to continue until the last enrolled patient reached 48 weeks on therapy.

Treatment Regimen

After initial screening, qualifying patients were randomly divided in three arms. Each patient in arm A was prescribed zidovudine (AZT) in 300 mg doses twice-daily, lamividine (3TC) 150 mg tablets twice-daily, and efavirenz (EFV) 600 mg dose once daily. Each patent in arm B received the same antiretroviral therapy plus the composition No. 1 of the present invention given as 50 drops added to a glass of water, twice-daily. The arm C patients received the same immunomodulator of the present invention as monotherapy in the same 50 drops twice-daily dose.

Evaluation

Parameters including as CD4 cell counts, AIDS defining events, relapse and new events of opportunistic infection (OI), adverse events, and laboratory parameters were assessed at baseline and at weeks 12, 20, and 32. For patients with clinical signs of adverse events laboratory tests were performed every two weeks. Baseline values for CD4 cells counts were defined as the average of the last screening and last baseline values. Adherence to treatment was assessed at each visit. Adverse events were graded by intensity and their relationship to the study medications. AIDS defining adverse events (as per 1993 Center for Disease Control definitions of AIDS) were recorded in the same way as all other adverse events. Laboratory abnormalities were graded.

Statistical Analysis

The primary outcome measure was CD4 cells count, levels of adherence, incidence of HIV related events, other adverse events, and laboratory abnormalities. The trial was designed to compare arm A with arms B and C at weeks 12, 20, 32 and 48, using the proportion of patients. All statistical tests were performed as on the intent-to-treat (ITT) population, which included all patients who took at least one dose of study medications. Patients who discontinued for any reason were considered as treatment failures. Tests were performed on the on-treatment (OT) population, which included only those patients with available evaluation at that time point. The safety evaluation included all patients who had at least one post-baseline safety assessment.

Change in CD4 Cell Counts

Significant increases from baseline were seen in all three arms at every assessed time point. By the end of first 12 weeks of treatment, CD4 cell counts changed as follows: in arm A reaching +122 cells/mm$^3$; in arm B decreasing but not significantly, −10 cells/mm$^3$; and in arm C increasing +36 cells/mm$^3$, but not in a significant manner. On the follow-up CD4 counts increased progressively in all arms, reaching +108, +85, and +103 cells/mm$^3$ by 20 weeks, and +102, +190 and +175 cells/mm$^3$ by 32 weeks, for arms A, B and C respectively (OT analysis).

There was a significant difference between arm A compared with arms B and C in terms of change in CD4 counts from baseline to week 12. In arm A CD4 cell counts increased significantly compared with arm B, in which cell counts decreased (A versus B; $p<0.04$) and with arm C, where the increase in CD4 count was not significant compared to baseline level (A versus C; $p<0.05$).

The first statistically significant increase in CD4 counts from baseline was observed in groups B and C at week 20. By week 32 progressive increase in CD4 cells in these two groups was higher than in arm A (B versus A; $p<0.05$, and C versus A; $p<0.05$).

Arm C had three patients in a terminal stage of AIDS and who had very low levels of CD4 cells count at baseline: 65, 64, and 128 cells/mm$^3$, respectively. After treatment initiation CD4 cells rose, reaching +15, +111 and +194 cells/mm$^3$ by 12 weeks, and +85, +103 and +1171 cells/mm$^3$ by 20 weeks. In parallel with rising CD4 cell counts these patients experienced progressive clinical improvement.

Adverse Events

Over 32 weeks of treatment significant differences were observed between arm A as compared with arms B and C in terms of overall incidents of adverse events. At least one adverse event, which possibly and probably was related to the study medications, was reported in 65, 24, and 5% of patients in arms A, B, and C respectively. Most clinical adverse events were mild—gastrointestinal symptoms were the most frequently reported adverse events. Over 32 weeks period, the most common adverse events considered as possibly related to study medication as well as those of moderate or severe intensity are shown in Table 2. There were clear differences between arms in the pattern or incidence of adverse events: the levels of diarrhea and nausea were significantly higher in arm A compared with arm B. In contrast, in arm C gastrointestinal symptoms were not observed throughout the study period. Occurrences of headache and fatigue also were significantly higher in arm A when compared with arm B and these symptoms were not observed in arm C. Seven patients (35%) in arm A experienced serious adverse events, which were considered to be possibly or probably related to study medication. In this arm 1 patient (5%) refused further therapy and 6 patients (30%) needed replacement therapy due to progressive fatigue, vomiting and gastrointestinal disorders, and/or hepatotoxicity. In arms B and C no incidents of interruption or changing therapy were observed. There were also significant differences between three arms in respect to laboratory findings (Table 2).

Opportunistic or Co-Infection Defined Events

During the 32 week reporting period, opportunistic infections (OI) were observed in all three arms under therapy. OI were observed in 6 (30%), 4 (13%) and 4 (20%) patients for A, B and C arms, respectively (Table 3). There was a clear distinction between treatment arms in terms of frequency OI and co-infection events. These events were significantly higher in arm A compared with arms B or C.

Among the most frequently reported relapses of OI and co-infection were oral or esophageal candidiasis 4 (20%), 2 (7%), and 2 (10%), herpetic infections 4 (20%), 4 (13%) and 3 (15%) patients in the arms A, B and C respectively. Acute tuberculosis was observed in 2 (10%) and 2 (7%) patients in arms A and B, respectively. Similarly, the relapses of hepatitis C were observed only in arms A and B, 2 (10%) and 1 (3%), respectively.

Effect on Liver Function

Most patients enrolled in study had underlying liver pathology. Signs of progressing chronic inflammatory process in liver caused by persistent viral infection, toxicity, and alcohol were registered as mean values of standard liver function test (LFT). Baseline ALT or/and AST were elevated in 7/20 (30%), 13/30 (43%), 11/20 (55%) patients in arms A, B, and C, respectively. Mean baseline values for ALT were 36, 62, and 72 U/L, respectively. The median cumulative change from baseline ALT values were +22, +18 and −16 U/L at 12 weeks, +30, −36, and −34 U/L by week 20, and +42, −24, −41 U/L by week 32 for arms A, B, and C, respectively. At week 32 ALT values have increased to a mean 78 U/L in arm A and declined to 38 and 31 U/L in arms B and C, respectively. The difference between arms B and C compared with arm A in terms of ALT values (B versus A; $p<0.05$, C versus A; $p<0.03$). In arm C ALT values were decreasing progressively under therapy and became significantly lower than baseline levels (P<0.01). Similar trends were observed with AST marker. The mean baseline values of AST were 42, 49, 58 U/L for arms A, B and C, respectively. At week 32 ALT values increased to a mean 68 U/L in arm A and decreased to 42 and 26 U/L in arms B and C, respectively. The number of patients with ART related hepatotoxicity was 6 (30%) and 2 (10%) patients in arm A and B respectively. In arm C no cases of drug-related hepatotoxicity were noted.

Effect on Body Weight

Mean values for baseline body weight were 64.2±8.9; 68.9±7.6; 67.3±8.4 kg for arms A, B, and C. Among arms A, B, and C 7 (35%), 11 (33%), 6 (30%) patients had cachexia. The body mass steadily increased during therapy, reaching 1.4; 6.9; and 5.1 kg gain at week 32 for arms A, B, and C, respectively. Weight gain varied for every patient ranging from 0.5-2 kg up to 6-9 kg during the therapy period. At the end of study, the mean weight values were 65.6±7.3; 75.8±6.9; 72.4±8.6 kg for arms A, B, and C respectively. Further results are shown below and in Table 4.

Several chemical anti-HIV agents have been developed. However, besides the high cost, there are adverse effects and toxicity associated with use of chemotherapy. Herbal medicines have frequently been used as alternative means of therapy by HIV positive individuals and AIDS patients. Except for a few instances, there is insufficient evidence to support the benefit of plant-derived medicines. Potential beneficial effects of medicinal plants need to be confirmed by rigorous clinical trials, preferably by comparing them to standard ART as in the present study.

The safety and efficacy of immunomodulator composition No. 1 of the present invention is compared to standard antiretroviral therapy AZT/3TC/EFV or combination of AZT/3TC/EFV with the composition of present invention using as the primary endpoint the change in CD4 lymphocyte counts. The increase from baseline in CD4 cells was seen in all three arms at every assessed time point. However, patients on standard ART therapy gained lowest number of cells when compared to B and C arms, i.e., +102, +190, and +175 cells/mm$^3$.

Additional parameters under consideration were the incidence of adverse events, frequency of opportunistic infections and co-infections, liver function test, and effect on body weight. The incidence of adverse events which possibly and probably were related to the study medications was lowest in the composition No. 1 of the present invention arm (5%) when compared to standard AZT/3TC/EFV tri-therapy (65%). Interestingly, patients in arm B who were both treated with AZT/3TC/EFV and the composition of present invention had significantly lower incidence (24%) of adverse events and hepatotoxicity despite exposure to the same ART dose as in arm A.

Surprisingly, the composition No. 1 of the present invention seems to normalize elevated liver enzyme levels. At treatment initiation baseline values for ALT were 36, 62, and 72 U/L but at week 32 ALT values have increased to a mean 78 U/L in arm A but declined to 38 and 31 U/L in B and C arms. These properties of the composition of present invention are of major consequence to management of ART toxicity. In addition to iatrogenic hepatotoxicity that ranges from mild hepatitis to liver failure there is a significant threat in form of chronic viral hepatitis, i.e., HCV and HBV with higher risk of morbidity and mortality. Almost half of patients participating in this trial had confirmed HCV infection. However, despite the lack of hepatitis-specific treatment, patients who were given composition No. 1 of the present invention, experienced normalization of initially high ALT and AST levels without a single incident of relapse. In contrast patients on AZT/3TC/EFV had higher incidence of hepatitis relapses. The patients on the same ART regimen supplemented with the composition of present invention had a lower number of outbreaks and a normalized liver function test. These observations indicate clearly that the composition No. 1 of the present invention possesses anti-inflammatory activity.

AIDS-associated wasting is the major factor that contributes to morbidity and mortality. Currently, there is no standard treatment for this condition, which remains poorly treatable even in countries with advanced medical care. Some nutritional regimens yield positive results, however their success has been unpredictable. Weight gain observed with the composition No. 1 of the present invention was significantly higher when compared to such supplements or ART therapy. This weight-correcting property alone represents a significant achievement that greatly augments the choice of available treatment options.

Currently, several immunotherapeutic approaches are available. So far most of these therapies are in the domain of so-called therapeutic vaccines and related immunotherapies. Very few validated, immune-based interventions are available when it comes to products of plant origin. Most studies in this area concern Oriental medicinal plants some of which were used for treatment of autoimmune disorders such as habitual abortion. However, there are no examples of application of autoimmunity-regulating herbs in infectious diseases, especially HIV infection. Not every herbal preparation can possess the right property suitable for such an indication. Indeed, some herbal supplements were shown to exacerbate autoimmunity—a property contrary to the intended action of the compositions of the present invention. On the other hand it would be a mistake to classify the composition No. 1 of the present invention as an immunosuppressant. The decrease in the frequency of opportunistic infections and absence of new episodes of OI as demonstrated in this trial, indicate that the composition No. 1 of the present invention does not compromise the immunity, whether acquired or native. These considerations are intriguing not only from the immunological point-of-view but are also important in finding effective therapeutic solutions for diseases which so far have been refractory to existing choices of treatment.

Thus, the composition No. 1 of the present invention displays a broad-spectrum clinical activity that has far-reaching implications. It reduces drug toxicity and improves ART efficacy when used in combination with standard ART. It enhances anti-HIV activity of ART. It enhances the anti-HIV activity of ART. Further studies are required to identify the mechanism of action and additional benefits associated with its use.

In addition to use of the composition No. 1 of the invention alone it is also contemplated to use it in combination with one or more compounds selected from the group consisting of HIV reverse transcriptase inhibitors, protease inhibitors, integrase inhibitors, fusion inhibitors, viral entry inhibitors, vaccines, therapeutic vaccines, and/or other known immunomodulators, as deemed necessary to a practicing physician skilled in the art. For example reverse transcriptase inhibitors can be selected from the group including nucleoside RT inhibitors: Retrovir (AZT/zidovudine; Glaxo Wellcome); Combivir (Glaxo Wellcome); Epivir (3TC, lamivudine; Glaxo Wellcome); Videx (ddI/didanosine; Bristol-Myers Squibb); Hivid (ddC/zalcitabine; Hoffmann-La Roche); Zerit (d4T/stavudine; Bristol-Myers Squibb); Ziagen (abacavir, 1592U89; Glaxo Wellcome); Hydrea (Hydroxyurea/HO; nucleoside RT potentiator from Bristol-Myers Squibb) or Non-nucleoside reverse transcriptase inhibitors (NNRTIs): Viramune (nevirapine; Roxane Laboratories); Rescriptor (delavirdine; Pharmacia & Upjohn); Sustiva (efavirenz, DMP-266; DuPont Merck); Preveon (adefovir dipivoxil, bis-POM PMEA; Gilead). Protease inhibitors (PI's) can be selected from Fortovase (saquinavir; Hoffmann-La Roche); Norvir (ritonavir; Abbott Laboratories); Crixivan (indinavir; Merck & Company); Viracept (nelfinavir; Agouron Pharmaceuticals); Angenerase (amprenavir/141W94; Glaxo Wellcome), VX-478, KNI-272, CGP-61755, and U-103017. Other inhibitors not listed here but from the families of drugs used in antiviral therapy are contemplated as well.

Example 4

Treatment of Tuberculosis Patients

Further studies were carried out on patients suffering from tuberculosis. The study parameters are provided in Tables 5-6 and results of the study are provided in Tables 7-9. Table 10 shows conclusions.

Open-label, salvage anti-tuberculosis therapy (ATT) combined with immunomodulators from medicinal plants, was conducted in 20 patients, comprising seven who had HIV co-infection. Excepting five patients with HIV, all other individuals had multidrug-resistant TB (MDR-TB) including 7 (35%) patients with XDR-TB. Patients hospitalized in a TB dispensary were treated TB drugs under directly observed therapy (DOT) until repeated negative culture conversion and recuperation from radiological and clinical symptoms. Three phytopreparations were used in addition to standard TB therapy as adjunct immunotherapy. The first had aqueous-alcohol extract from medicinal plants from composition No. 2, set No. 1. The second preparation was composition no. 2, set No. 2. The third multi-herb composition was composition No. 2, set No. 3.

The duration of treatment ranged between 10.6–30.3 weeks with average/median 16.2/16 weeks (Table 10). The treatment lasted until patients were discharged from the dispensary upon twice-repeated negative culture findings and clinical and radiological improvements. The time to negative culture conversion ranged between 9-62 days with mean/median 30.6/30 days. Mycobacterial clearance was confirmed by repeated cultures at monthly intervals.

There was no difference between chronic, previously treated TB versus first-diagnosed TB cases in terms of days to discharge, i.e., 111.6 vs 114.8 ($p=0.42$) or days to mycobacterial clearance, 33.7 vs 28 ($p=0.16$). A similar stratification analysis comparing TB/HIV with TB alone patients reveals that patients with dual infection appear to require longer treatment, i.e., 127.9 vs 105.5 days, but the difference was not statistically significant ($p=0.15$). Similarly, negative culture conversion occurred about nine days later in TB/HIV individuals than in TB patients, i.e., 36.1 vs 27.5 days, but the difference was not statistically reliable ($p=0.08$). The comparison of treatment outcomes between 15 drug-resistant and 5 drug-sensitive cases also failed to reveal statistical difference. Time to negative culture was 30.3 vs 31.4 days and time to discharge 106.2 vs 134.8 days with probability values $p=0.4$ and $p=0.18$ respectively. These finding indicate that when ATT is combined with the composition No. 2 herbals its efficacy is enhanced since normally ATT is not effective when patients with drug-resistant TB and/or HIV are treated.

At the end of study almost every patient had gained substantial lean body mass—an effect that was evident within one month from initiation of the therapy. One TB/HIV patient (#19) lost 10 kg, but all other patients gained weight, ranging between 3 and 17 kg. The average accrual in lean body mass was 8.7 kg (median 9.5 kg), which was statistically highly significant as evidenced by paired Student t-test ($p=0.0000008$).

The potential hepatotoxicity of ATT when used in combination with herbal preparations was monitored by quantitative liver function tests. Surprisingly, despite intensive chemotherapy, patients have shown signs of better liver function. The level of total bilirubin had decreased from mean 15.5 to 11.6 μmol/L—a favorable change that was statistically significant ($p=0.009$). Similarly, the values of alanine transaminase (ALT), another marker of liver damage, declined from abnormally high (53.1 IU/L) to normal levels (30.4 IU/L)—a change that was also statistically significant ($p=0.01$).

Another phenomenon observed during therapy is a reversal of the baseline anemic state and pro-inflammatory condition—which are symptoms very common in TB and HIV. Most patients at study entry displayed signs of anemia and had abnormally elevated leukocyte counts. At the end of treatment these parameters were improved in a statistically significant manner. The levels of hemoglobin had risen from 103.2 to 117.3 g/L ($p=0.00005$), whereas leukocyte counts returned back to normal levels from 8.9 to $6.9 \times 10^9$ cells/L ($p=0.003$).

Flow cytometry measurements of T lymphocyte counts conducted at study entry and at the end of follow-up were available in 6 of 7 TB/HIV patients. The helper CD4+ cells declined in two patients, while the remaining patients displayed an increase in their lymphocyte numbers. When calculated for the total population there was an increase at the end of the study compared to baseline levels. From an average of 371 cells/μl at baseline they have risen to 566 cells/μl—an increase equal to 52% ($p=0.07$). The absolute numbers of CD8+ T-lymphocytes appeared to decline but no statistical significance was reached ($p=0.1$). The increase in CD4 cells and decline in CD8 cells resulted in an almost doubled ratio of CD4/CD8 cells, i.e., from baseline 0.475 to 0.848 at the end of study ($p=0.03$). See FIG. 1. FIG. 1 shows changes in T-lymphocytes in absolute and percentage terms in patients with TB and HIV. The patients in Arm A of the study received TB drug treatment only, for two months. The patients in Arm B of the study received TB drug treatment and the herbal immunomodulator No. 2 of the invention, for two months.

The composition No. 2 of the invention may be useful not only for HIV and TB as demonstrated convincingly above but for treatment of other ailments as well. Besides being useful for human treatment, these compounds are also useful for veterinary and lab animal use, including horses, dogs, cats, rats, mice, sheep, and pigs.

TABLE 1

Summary of HIV+ patients at study initiation

| | Arm A (N = 20) AZT/3TC/EFV 600/300/600 mg daily N(%) | Arm B (N = 30) AZT/3TC/EFV + Composition of present invention 600/300/600 mg + 100 drops daily N(%) | Arm C (N = 20) Composition of present invention 100 drops daily N(%) |
|---|---|---|---|
| Characteristics | | | |
| Male | 8(40%) | 18(59%) | 16(80%) |
| Female | 12(60%) | 12(41%) | 4(20%) |
| Body weight Mean ± SD | 64.2 ± 8.9 kg | 68.9 ± 7.6 kg | 67.3 ± 8.4 kg |
| CD4 cell counts (cells/mm$^3$) | 361 | 421 | 462 |
| Prior antiretroviral therapy (%) | 0 | 0 | 0 |
| Patients with TB | 7(35%) | 7(23%) | 9(45%) |
| Hepatitis C or B | 9(45%) | 11(33.3%) | 12(50%) |
| Oral or esophageal candidiasis | 7(35%) | 19(62.7%) | 15(75%) |
| Herpes zoster | 5(25%) | 7(23%) | 11(55%) |

TABLE 1-continued

Summary of HIV+ patients at study initiation

|  | Arm A (N = 20) AZT/3TC/EFV 600/300/600 mg daily N(%) | Arm B (N = 30) AZT/3TC/EFV + Composition of present invention 600/300/600 mg + 100 drops daily N(%) | Arm C (N = 20) Composition of present invention 100 drops daily N(%) |
|---|---|---|---|
| Laboratory shift abnormalities | | | |
| ↓ Neutrophils | 1(5%) | 2(7%) | |
| ↑ Aspartate aminotransferase | 6(30%) | 11(33%) | 7(35%) |
| ↑ Alanine aminotransferase | 7(35%) | 9(29%) | 8(40%) |
| ↓ Hemoglobin | 2(10%) | 2(7%) | 1(5%) |

TABLE 2

Percentage of patients with clinical adverse events considered as possibly related to treatment and of moderate or severe intensity.

| Adverse events | Arm A (N = 20) AZT/3TC/EFV 600/300/600 mg daily N(%) | Arm B (N = 30) AZT/3TC/EFV + Composition of the present invention 600/300/600 mg + 100 drops daily N(%) | Arm C (N = 20) the composition of present invention monotherapy 100 drops daily N(%) |
|---|---|---|---|
| Diarrhea | 6(30%) | 2(7%) | |
| Nausea | 7(35%) | 2(7%) | |
| Vomiting | 2(10%) | | |
| Abdominal pain | 7(35%) | 3(10%) | |
| Headache | 3(15%) | 1(3%) | 1(5%) |
| Peripheral neuropathy | | | |
| Fatigue | 11(55%) | 3(10%) | 1(5%) |
| Laboratory abnormalities | | | |
| ↓ Neutrophils | 2(10%) | | |
| ↑ Aspartate aminotransferase | 5(25%) | 1(3%) | |
| ↑ Alanine aminotransferase | 6(30%) | 2(6%) | |
| ↓ Haemoglobin | 2(10%) | | |
| ↑ Cholesterol | 2(10%) | | |

TABLE 3

Percentage of patients presenting with clinical OI or co-infection defined events during 32 weeks treatment period

| OI and co-infections | Arm A (N = 20) AZT/3TC/EFV 600/300/600 mg daily N(%) | Arm B (N = 30) AZT/3TC/EFV + the composition No. 1, 100 drops daily N(%) | Arm C (N = 20) composition No. 1, 100 drops daily N(%) |
|---|---|---|---|
| Oral/esophageal candidiasis | 4(20%) | 2(7%) | 2(10%) |
| Herpes | 4(20%) | 4(13%) | 3(15%) |
| Tuberculosis | 2(10%) | 2(7%) | |
| Cachexia | 3(15%) | | |
| Hepatitis C | 2(10%) | 1(3%) | |

TABLE 4

| Patients | CD4 counts | | ALT values | | Body weight | |
|---|---|---|---|---|---|---|
| | Before | After | Before | After | Before | After |
| Arm A | 361 | 463 | 36 U/L | 78 U/L | 64.2 | 65.6 |
| Arm B | 421 | 611 | 62 U/L | 38 U/L | 68.9 | 75.8 |
| Arm C | 462 | 637 | 72 U/L | 31 U/L | 67.3 | 72.4 |

TABLE 5

Effect of therapy with antiviral drugs (ART) without or with herbal composition on HIV-RNA plasma levels

| Patient No. | Arm A HIV patients on ART alone (N = 20) | | | Arm B HIV patients on ART + Herbal composition (N = 20) | | |
|---|---|---|---|---|---|---|
| | HIV-RNA copies/ml at baseline | HIV-RNA copies/ml at $2^{nd}$ month | Difference compared to baseline | HIV-RNA copies/ml at baseline | HIV-RNA copies/ml at $2^{nd}$ month | Difference compared to baseline |
| 1 | 847.2 | 473.5 | −373.7 | 952.2 | 421.2 | −531 |
| 2 | 1756.8 | 1308.3 | −448.5 | 1353.0 | 789.1 | −563.9 |
| 3 | 978.1 | 1123.6 | +145.5 | ND | ND | ND |
| 4 | 2564.3 | 1141.2 | −1423.1 | 3899.1 | 1854.4 | −2044.7 |
| 5 | 345.4 | 96.1 | −249.3 | 818.4 | 379.1 | −439.3 |
| 6 | 2053.0 | 1845.1 | −207.9 | 1938.0 | 956.3 | −981.7 |
| 7 | 763.2 | 1295.1 | +531.9 | 2501.4 | 2296.1 | −205.3 |
| 8 | 1537.0 | 867.1 | −669.9 | 783.5 | 1394.6 | +611.1 |
| 9 | 894.2 | 778.0 | −116.2 | 464.3 | 235.1 | −229.2 |
| 10 | 7442.1 | 7601.4 | +159.3 | 937.3 | 562.1 | −375.2 |
| 11 | 346.4 | 189.3 | −157.1 | 1558.1 | 1415.4 | −142.7 |
| 12 | 3178.2 | 2723.1 | −455.1 | 10136.5 | 10112.1 | −24.4 |
| 13 | 237.0 | 91.3 | −145.7 | 539.0 | 241.3 | −297.7 |
| 14 | 881.3 | 922.4 | +41.1 | 669.4 | 314.2 | −355.2 |
| 15 | 1045.0 | 851.1 | −193.9 | 1749.4 | 958.2 | −791.2 |
| 16 | 2339.3 | 1911.0 | −428.3 | 973.6 | 689.1 | −284.5 |
| 17 | 473.1 | 529.4 | +56.3 | 889.7 | 564.2 | −325.5 |
| 18 | 3088.2 | 2064.3 | −1023.9 | 2377.1 | 1918.4 | −458.7 |
| 19 | ND | ND | ND | 254.5 | 99.4 | −155.1 |
| 20 | 1865.5 | 1141.1 | −724.4 | 1271.3 | 788.3 | −483 |
| Statistics | Mean ± SD = 1717 ± 1660 Geometric mean = 1199 Median = 1045 | Mean ± SD = 1419 ± 1650 Geometric mean = 876 Median = 1124 | Mean ± SD = −299 ± 448 Geometric mean = 272 Median = −208 Wilcoxon signed rank test; P = 0.008 | Mean ± SD = 1792 ± 2202 Geometric mean = 1222 Median = 974 | Mean ± SD = 1368 ± 2208 Geometric mean = 762 Median = 788 | Mean ± SD = −425 ± 507 Geometric mean = 353 Median = −355 Wilcoxon signed rank test; P = 0.001 |

ND: not done

TABLE 6

Effect of two separate treatments on body weight in patients with TB

| TB/HIV Patients | Body weight prior to therapy (kg ± SD) | Proportion of patients with cachexia | Weight change after 6 months on therapy |
|---|---|---|---|
| TB drugs + composition No. 2 (n = 20) | 52 ± 5.7 | −8.5 ± 2.7 (n = 12) | +2.7 kg |
| TB drugs (n = 20) | 64 ± 6.3 | −5.2 ± 1.7 (n = 13) | −0.6 kg |

TABLE 7

Results of treatment of drug-resistant TB patients.

| Drug-resistant TB patients | Time to negative culture in sputum | Negative culture | Response to therapy by radiology | |
|---|---|---|---|---|
| | | | New TB diagnosis | Chronic TB form |
| TB drugs + composition No. 2 (n = 40) | 3.5-4 months | 80% | 89% | 70% |
| TB drugs (n = 40) | 5.8-6 months | 30% | 29% | 10% |

TABLE 8

Culture and radiological findings in TB/HIV co-infected patients

| TB/AIDS patient Groups | Culture negative 2nd month | Culture negative 3rd month | Healing of cavities 3rd month |
|---|---|---|---|
| TB drugs + composition No. 2 (n = 33) | 64 ± 8% | 82 ± 7% | 36 ± 8% |
| TB drugs (n = 33) | 18 ± 8% | 21 ± 7% | 3 ± 3% |

TABLE 9

Effect on culture conversion and cavitary and miliary forms of TB

| | Arm A (n = 20): ATT | | | | Arm B (n = 20): ATT + Herbal composition No. 2 | | | | |
|---|---|---|---|---|---|---|---|---|---|
| Primary Endpoints | Patients at baseline | Responders | Time (weeks) | Percent of response | Patients at baseline | Responders | Time (weeks) | Percent of response | P value |
| Smear and culture findings | 19 | New 3 Chronic 0 | 20-24 | 16% | 18 | New 9 Chronic 3 | 16 24 | 67% | 0.003 |
| Cavitary and destructive TB | 16 | 40 | 24-28 | 25% | 15 | 9 | 16-18 | 60% | 0.025 |
| Miliary and infiltrating TB | 15 | 7 | 24-28 | 46% | 13 | 11 | 16-18 | 84% | 0.046 |

TABLE 10

Characteristics of TB patients treated with ATT in combination with herbals

| No. | Sex | Age | TB infection | TB drug resistance* | HIV status/ AIDS stage | Days on DOT | Days to negative culture | Leukocyte × $10^9$ L before | after |
|---|---|---|---|---|---|---|---|---|---|
| 1/54 | M | 30 | Primary | MDR H/R/Z/O | — | 74 | 10 | 9.4 | 12 |
| 2/57 | M | 58 | Primary | MDR R/ETH CPX/PFX | — | 122 | 30 | 9.8 | 6 |
| 3/73 | M | 38 | Chronic | MDR S/H/ETH PAS | — | 131 | 30 | 14 | 6 |
| 4/78 | F | 40 | Primary | MDR H/R/K PAS Prothio | — | 77 | 9 | 10 | 5.2 |
| 5/92 | M | 32 | Primary | MDR H/E/PAS/ RFB | — | 122 | 55 | 5.8 | 6 |
| 6/492 | M | 47 | Chronic | MDR H/R/E/K | — | 75 | 28 | 8 | 6.8 |
| 7/56 | M | 42 | Primary | XDR H/R/E K/O/PAS | — | 74 | 23 | 11.6 | 8.1 |
| 8/64 | M | 47 | Primary | XDR H/R/S/K L/PFX | — | 133 | 22 | 9.1 | 9.1 |
| 9/68 | M | 52 | Primary | XDR H/R/A PFX/PAS | — | 117 | 37 | 11 | 6 |
| 10/84 | M | 44 | Primary | XDR H/R/ETH K/L/PAS | — | 143 | 34 | 4.5 | 6.8 |
| 11/156 | M | 25 | Chronic | XDR H/R/Z/K O/A/PAS | — | 89 | 25 | 8.2 | 6 |
| 12/532 | M | 48 | Chronic | XDR H/R/K/A O/PAS | — | 122 | 35 | 8.8 | 5.3 |
| 13/627 | M | 35 | Primary | XDR H/R/K/A CPX/PFX | — | 93 | 20 | 9 | 10 |

TABLE 10-continued

Characteristics of TB patients treated with ATT in combination with herbals

| No. | Sex | Age | | | | | | | |
|---|---|---|---|---|---|---|---|---|---|
| 14/59 | M | 47 | Primary | — | +/III | 212 | 34 | 6.8 | 6.9 |
| 15/61 | M | 39 | Chronic | — | +/III | 107 | 38 | 6.5 | 4.9 |
| 16/161 | F | 34 | Chronic | — | +/III | 98 | 34 | 5.4 | 5.2 |
| 17/185 | F | 24 | Chronic | — | +/III | 74 | 24 | 6.5 | 7.3 |
| 18/295 | M | 45 | Chronic | — | +/III | 183 | 27 | 9 | 6.8 |
| 19/72 | M | 27 | Chronic | MDR H/K/A/PAS | +/III | 125 | 62 | 11 | 6.2 |
| 20/481 | F | 39 | Primary | MDR H/R/K Prothio | +/III | 96 | 34 | 13.3 | 7.1 |
| sum | 4/16 | 39.7 ± 9.2 | 9/11 | 5/15 | 7/13 | 113.4 ± 36.7 | 30.6 ± 12.5 | 8.9 ± 2.5 Mean decrease = $2 \times 10^9$ L $P = 0.003$ | 6.9 ± 1.8 Mean gain = 14.1 g/L $P = 0.00005$ |

| No. | Hb g/L | | Weight change kg | | Total bilirubin | | ALT IU/L | |
|---|---|---|---|---|---|---|---|---|
| | before | after | before | after | before | after | before | after |
| 1/54 | 82 | 104 | 60 | 68 | 32.4 | 11.7 | 37 | 50 |
| 2/57 | 120 | 123 | 66 | 78 | 14 | 10.5 | 37 | 50 |
| 3/73 | 108 | 120 | 52 | 68 | 16.3 | 10.5 | 62 | 12 |
| 4/78 | 100 | 116 | 52 | 56 | 14 | 10.5 | 25 | 12 |
| 5/92 | 110 | 122 | 75 | 85 | 10.5 | 10.7 | 50 | 12 |
| 6/492 | 106 | 122 | 66 | 78 | 14 | 19.7 | 75 | 50 |
| 7/56 | 122 | 114 | 59 | 68 | 10.5 | 11.7 | 25 | 50 |
| 8/64 | 108 | 116 | 52 | 62 | 11.7 | 10.7 | 62 | 12 |
| 9/68 | 100 | 118 | 64 | 74 | 11.7 | 10.4 | 75 | 12 |
| 10/84 | 120 | 118 | 63 | 69 | 18.6 | 10.5 | 12 | 50 |
| 11/156 | 109 | 120 | 65 | 78 | 10.5 | 10.5 | 62 | 12 |
| 12/532 | 88 | 122 | 72 | 78 | 14 | 10.5 | 37 | 12 |
| 13/627 | 88 | 118 | 50 | 63 | 32.4 | 10.5 | 25 | 12 |
| 14/59 | 128 | 118 | 77 | 80 | 11.7 | 10.5 | 50 | 50 |
| 15/61 | 106 | 112 | 65 | 76 | 10.5 | 11.5 | 75 | 50 |
| 16/161 | 105 | 118 | 58 | 67 | 20.9 | 10.5 | 42 | 12 |
| 17/185 | 95 | 118 | 63 | 70 | 10.5 | 10.5 | 75 | 50 |
| 18/295 | 94 | 120 | 61 | 68 | 18.6 | 18.6 | 112 | 50 |
| 19/72 | 102 | 116 | 76 | 66 | 16.4 | 10.5 | 37 | 12 |
| 20/481 | 72 | 110 | 43 | 60 | 11.7 | 10.5 | 87 | 37 |
| sum | 103.2 ± 14 | 117.3 ± 4.6 Mean gain = 8.7 kg $P = 0.000009$ | 61.9 ± 9.1 Mean decrease = 3.9 μmol/L $P = 0.009$ | 70.6 ± 7.5 Mean decrease = 22.7 IU/L $P = 0.001$ | 15.5 ± 6.5 | 11.6 ± 2.6 | 53.1 ± 27 | 30.4 ± 17.5 |

*Criteria for definition of XDR are as per WHO recommendation. ATT drugs are abbreviated as follows: Isoniazid (H), Rimfapicin (R), Pyrazinamide (Z), Ethambutol (E), Streptomycin (S), Levofloxacin (L), Ofloxacin (O), Ciprofloxacin (CPX), Pefloxacin (PFX), Kanamycin (K), Amikacin (A), Paraaminosalicylic acid (PAS), Rifabutin (RFB), Ethionamide (ETH), Prothionamide (Prothio)

I claim:

1. A composition consisting essentially of an alcohol-water extract of plant material from Aloe (*Aloe arborescens*), Common knotgrass (*Polygonum aviculare*), Yarrow (*Achillea millefolium*), Purple coneflower (*Echinacea purpurea*), St. John's Wort (*Hypericum perforatum*), Centaury (*Centaurium erythraea*), Snowball tree berries (*Viburnum opulus*), Nettle (*Urtica dioica*), Dandelion (*Taraxacum officinale*), Sweet-sedge (*Acorus calamus*), Oregano (*Origanum vulgare*), Marigold (*Calendula officinalis*), Seabuckthorn berries (*Hippophae rhamnoides*), Elecampane (*Inula helenium*), Tormentil (*Potentilla erecta*), Greater plantain (*Plantago major*), Wormwood (*Artemisia* sp.), Siberian golden root (*Rhodiola rosea*), Cudweed (*Gnaphalium uliginosum*), Licorice (*Glycyrrhiza glabra*), Fennel (*Foeniculum vulgare*), Chaga (*Inonotus obliquus*), Thyme (*Thymus vulgaris*), Three-lobe Beggarticks (*Bidens tripartite*), Sage (*Salvia officinalis*), Dog rose (*Rosa canina*), Juniper berries (*Juniperus communis*), Barberry roots (*Berberis vulgaris*), Chicory roots (*Cichorium intybus*), Coriander seeds (*Coriandrum sativum*), Maize cores with stigmas (*Zea mays*), Aronia berries (*Aronia melanocarpa*), Wild strawberry leaves (*Fragaria vesca*), Greater celandine (*Chelidonium majus*), and Immortelle (*Helichrysi arenarii*).

* * * * *